US010001458B2

(12) United States Patent
Kobayashi et al.

(10) Patent No.: US 10,001,458 B2
(45) Date of Patent: Jun. 19, 2018

(54) EDDY CURRENT FLAW DETECTION DEVICE, EDDY CURRENT FLAW DETECTION METHOD, AND EDDY CURRENT FLAW DETECTION PROGRAM

(71) Applicant: KABUSHIKI KAISHA TOSHIBA, Minato-Ku (JP)

(72) Inventors: Noriyasu Kobayashi, Yokohama (JP); Souichi Ueno, Ota (JP); Hiroya Ichikawa, Yokohama (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 116 days.

(21) Appl. No.: 14/781,851

(22) PCT Filed: Mar. 14, 2014

(86) PCT No.: PCT/JP2014/056898
§ 371 (c)(1),
(2) Date: Jan. 8, 2016

(87) PCT Pub. No.: WO2014/142306
PCT Pub. Date: Sep. 18, 2014

(65) Prior Publication Data
US 2016/0123928 A1 May 5, 2016

(30) Foreign Application Priority Data

Mar. 14, 2013 (JP) ................. 2013-052097
Jul. 12, 2013 (JP) ................. 2013-146262

(51) Int. Cl.
*G01N 27/00* (2006.01)
*G01N 27/90* (2006.01)

(52) U.S. Cl.
CPC ....... *G01N 27/902* (2013.01); *G01N 27/9033* (2013.01)

(58) Field of Classification Search
CPC .................. G01N 27/902; G01N 27/9033
See application file for complete search history.

(56) References Cited

U.S. PATENT DOCUMENTS 5,418,457 A * 5/1995 Hedengren ........ G01N 27/9053
324/225
2003/0132748 A1 * 7/2003 Hiroshima ......... G01N 27/9033
324/240

(Continued)

FOREIGN PATENT DOCUMENTS

JP  60 260801     12/1985
JP  2001 59836    3/2001

(Continued)

OTHER PUBLICATIONS

Extended European Search Report dated Dec. 6, 2016 in Patent Application No. 14764698.8.

(Continued)

*Primary Examiner* — Julian Huffman
*Assistant Examiner* — Michael Konczal
(74) *Attorney, Agent, or Firm* — Oblon, McClelland, Maier & Neustadt, L.L.P.

(57) ABSTRACT

There is provided an eddy current flaw detection technique capable of, even when inspecting an object having a narrow portion with a small curvature radius, recognizing detection sensitivity change due to change of attitude of a probe.
An eddy current flaw detection apparatus 10 includes: an AC power source 14 which generates an excitation magnetic field in each of excitation coils 12*a* accommodated in a probe 11 to excite an eddy current in an inspection object 13; a detecting section 15 which detects a detection signal generated by an induction magnetic field induced by the eddy current in each of detection coils 12 accommodated in the probe 11; an output section 16 which outputs flaw detection data based on the detection signals; a storage (Continued)

section 17 which mutually associates and stores the detection signals detected at the same timing from the plurality of coils 12*b*; and an evaluating section 18 which evaluates an attitude of the probe 11 based on the plurality of detection signals detected at the same timing and associated with each other.

6 Claims, 7 Drawing Sheets

(56) References Cited

U.S. PATENT DOCUMENTS

| | | | | |
|---|---|---|---|---|
| 2009/0242200 A1* | 10/2009 | Badoux | ............... | G01N 27/9033 |
| | | | | 166/255.2 |
| 2012/0025816 A1* | 2/2012 | Lepage | ................ | G01N 27/904 |
| | | | | 324/240 |

FOREIGN PATENT DOCUMENTS

| | | |
|---|---|---|
| JP | 2001 336905 | 12/2001 |
| JP | 2005-121506 A | 5/2005 |
| JP | 2010 122199 | 6/2010 |
| JP | 2010 281762 | 12/2010 |

OTHER PUBLICATIONS

Javier Garcia-Martin et al. "Non-destructive techniques based on eddy current testing", Sensors, vol. 11, No. 3, XP002718104, Feb. 28, 2011, pp. 2525-2565.

International Search Report dated Jun. 10, 2014 in PCT/JP2014/056898 Filed Mar. 14, 2014.

* cited by examiner

| FLAW DETECTION METHOD | SELF-INDUCTION | | MUTUAL INDUCTION |
|---|---|---|---|
| MEASUREMENT | COIL A AMPLITUDE (V) | COIL B AMPLITUDE (V) | COIL B PHASE ANGLE CODE |
| DIRECTION a | α | γ | POSITIVE |
| DIRECTION b | β | β | NEGATIVE |
| DIRECTION c | γ | α | POSITIVE |
| DIRECTION d | β | β | POSITIVE |
| DIRECTION e | α | γ | NEGATIVE |
| DIRECTION f | β | β | NEGATIVE |
| DIRECTION g | γ | α | NEGATIVE |
| DIRECTION h | β | β | POSITIVE |

EDDY CURRENT FLAW DETECTION DEVICE, EDDY CURRENT FLAW DETECTION METHOD, AND EDDY CURRENT FLAW DETECTION PROGRAM

TECHNICAL FIELD

Embodiments of the present invention relate to an eddy current flaw detection technique for non-destructively detecting a flaw, such as a crack, which exists in an inspection object.

BACKGROUND ART

As a method for detecting a flaw, such as a crack, which exists in a vicinity of a surface of a metal, an eddy current flaw detection apparatus has been used.

The eddy current flaw detection apparatus is configured such that an eddy current is generated on the surface of an inspection object by applying, to the inspection object, an excitation magnetic field from an excitation coil connected to an AC power source, and such that an induction magnetic field induced by the eddy current is detected by a detection coil.

With the eddy current flaw detection apparatus, a flaw in the inspection object is detected in such a manner that a probe configured by the excitation coil and the detection coil is scanned on the surface of the inspection object, and that a change of the eddy current due to a flaw (crack) which exists in the surface of the inspection object is detected as a change of the induction magnetic field.

Meanwhile, in order to detect a flaw with high sensitivity, it is necessary that the probe be scanned while the probe axis is made to coincide with the normal of the surface of the inspection object.

When the probe inclines during the scanning, the sensitivity of detecting the flaw is reduced, and further, a ghost may be detected.

In order to cope with this, there has been proposed a technique in which, in a test for detecting a flaw in a complicated-shaped surface having a three-dimensional shape change, the probe which is scanned is imaged so that the attitude of the probe is monitored (see, for example, Patent Document 1).

PRIOR ART DOCUMENTS

Patent Document

Patent Document 1: Japanese Patent Laid-Open No. 2012-181097

SUMMARY OF THE INVENTION

Problems to be Solved by the Invention

However, in the technique according to Patent Document 1, it cannot be said that there is a matching relationship between the probe attitude acquired from the result obtained by imaging the probe scanned on the complicated-shaped surface, and the sensitivity of the output signal of the coil. Therefore, the technique has a problem that the reliability thereof is low.

The present invention has been made in view of the above-described circumstances, and an object of the invention is to provide an eddy current flaw detection technique capable of, even when inspecting an object having a narrow portion with a small curvature radius, recognizing detection sensitivity change due to change of attitude of the probe.

Means for Solution to Problems

An eddy current flaw detection apparatus according to an embodiment of the present invention includes: an AC power source which generates an excitation magnetic field in each of excitation coils accommodated in a probe to excite an eddy current in an inspection object; a detecting section which detects a detection signal generated, by an induction magnetic field induced by the eddy current, in each of detection coils accommodated in the probe; an output section which outputs flaw detection data based on the detection signals; a storage section which mutually associates and stores the detection signals detected at a same timing from the plurality of detection coils; and an evaluating section which evaluates an attitude of the probe based on the plurality of detection signals detected at the same timing and associated with each other.

DESCRIPTION OF EMBODIMENTS

First Embodiment

In the following, embodiments of the present invention will be described with reference to the accompanying drawings.

Figure 1:
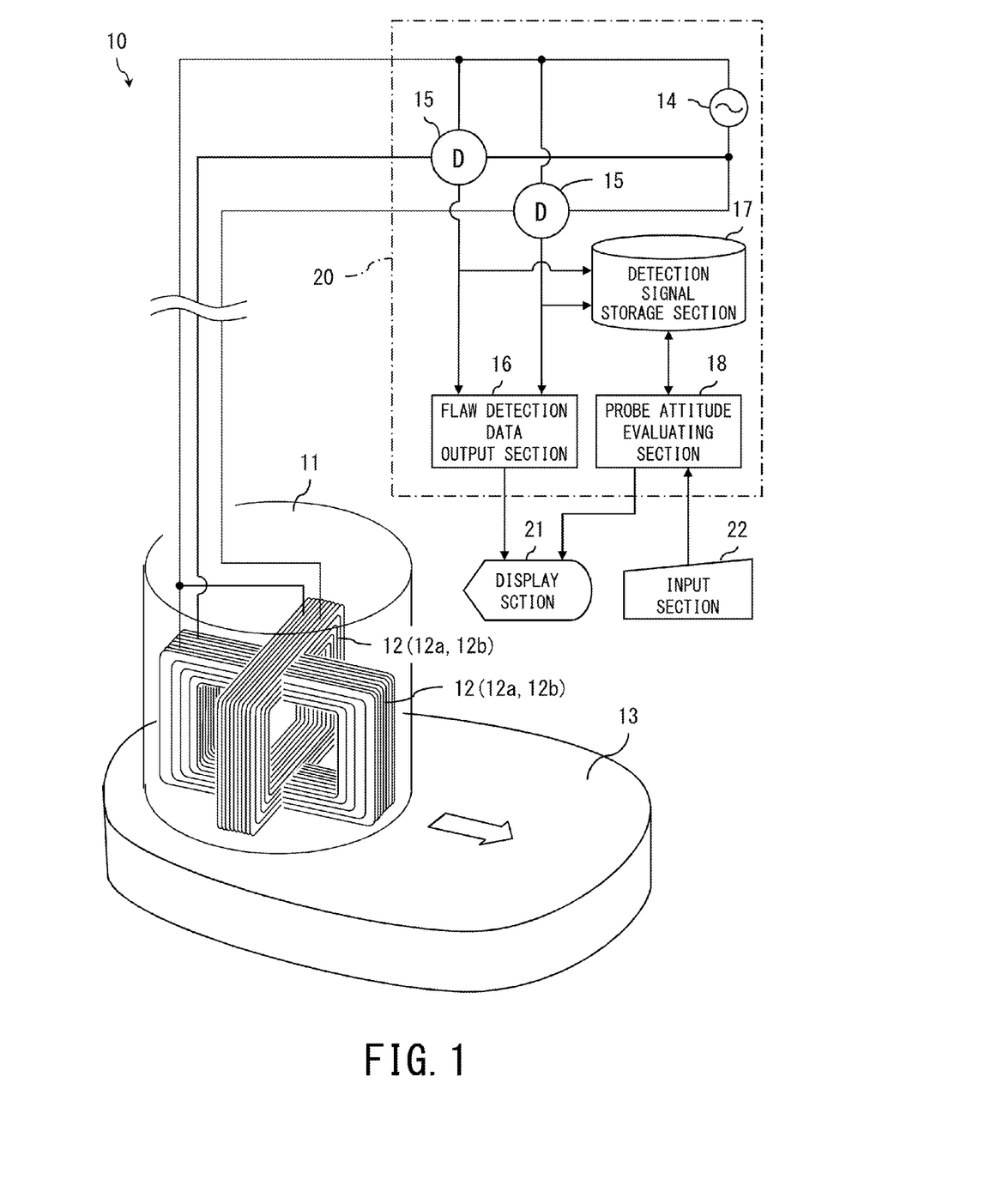
FIG. 1 is a schematic diagram showing a first embodiment of an eddy current flaw detection apparatus according to the present invention.

As shown in FIG. 1, a detection unit 20 of an eddy current flaw detection apparatus includes: an AC power source 14 which generates an excitation magnetic field in each of excitation coils 12a accommodated in a probe 11 and thereby excites an eddy current in an inspection object 13; a detecting section 15 which detects a detection signal generated by an induction magnetic field induced by the eddy current in each of detection coils 12b accommodated in the probe 11; an output section 16 which outputs fault detection data based on the detection signals; a storage section 17 which mutually associates and stores detection signals detected from the plurality of detection coils 12b at a same timing; and an evaluating section 18 which evaluates the attitude of the probe 11 based on the plurality of detection signals detected at the same time and associated with each other.

The eddy current flaw detection apparatus 10 configured in this way can be applied to the inspection of flaws in the inspection object 13 which is a metal structural material.

As the inspection object 13, it is possible to use a narrow shaped portion, such as a welding portion of a structure in a nuclear reactor, and a tube curved portion of a nuclear reactor nozzle stub.

In the embodiment is realized by a self-induction method in which the excitation coil 12a and the detection coil 12b are formed as one coil 12.

Figure 4A:
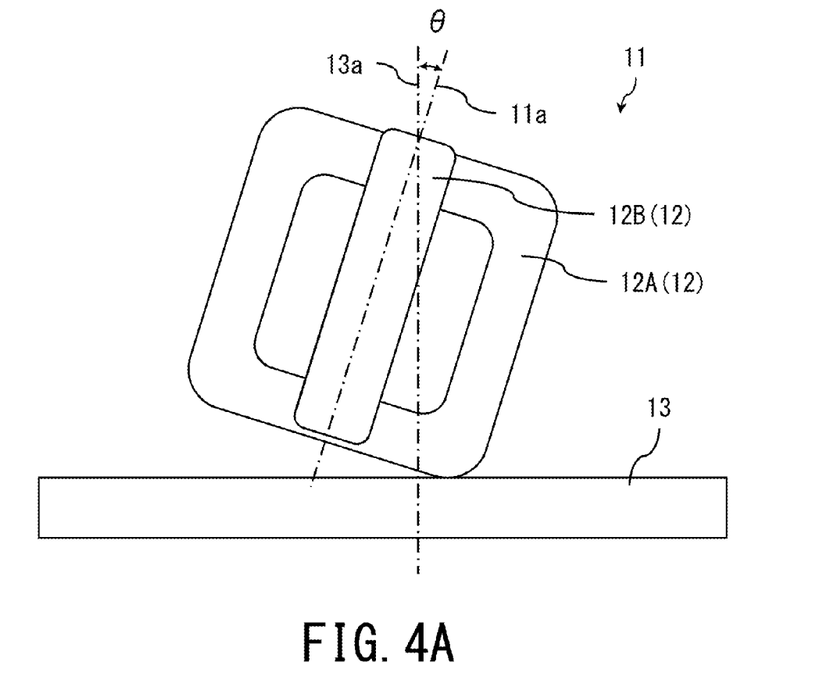
FIG. 4A is a side view of the coil for explaining the attitude of the probe.

The plurality of coils 12 and 12 (two in FIG. 1) are configured such that the central axes thereof, around which element wires are wound, perpendicularly intersect an axis 11a of the probe (see FIG. 4(A)) and further intersect at right angles to each other. The coils 12 and 12 are provided at the distal end of the probe 11.

The probe 11 is scanned on the surface of the inspection object 13 so that a surface normal 13a of the inspection object 13 and the probe axis 11a coincide with each other (so that an inclination angle θ=0) as much as possible (see, for example, FIG. 4(A)).

The coil 12 is configured such that band-shaped bodies, each formed by winding an element wire in one direction, are laminated together. Further, the portion, at which the two coils 12 intersect each other, is configured such that the band-shaped bodies of one of the two coils 12 are alternately laminated with the band-shaped bodies of the other of the two coils 12.

Figure 2A:
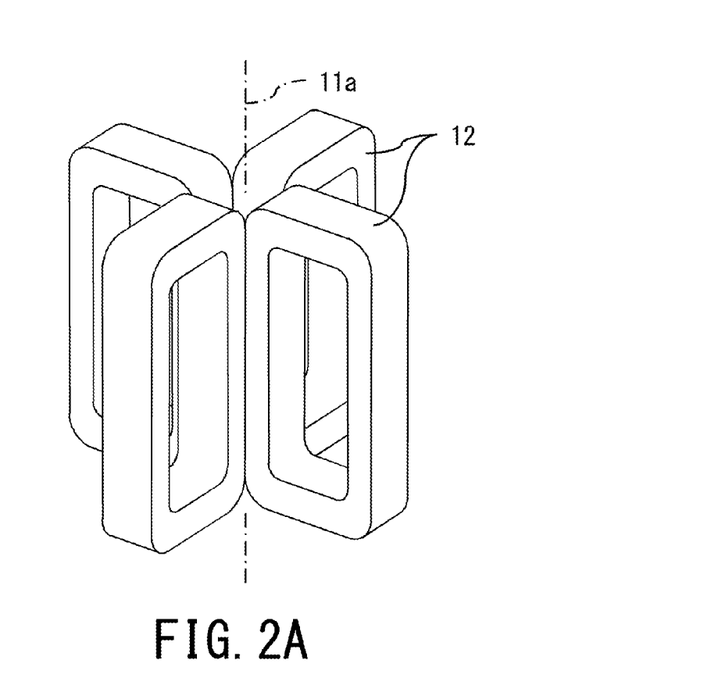
FIG. 2A and FIG. 2B each is a perspective view showing another embodiment of a coil provided in a probe.
Figure 2B:
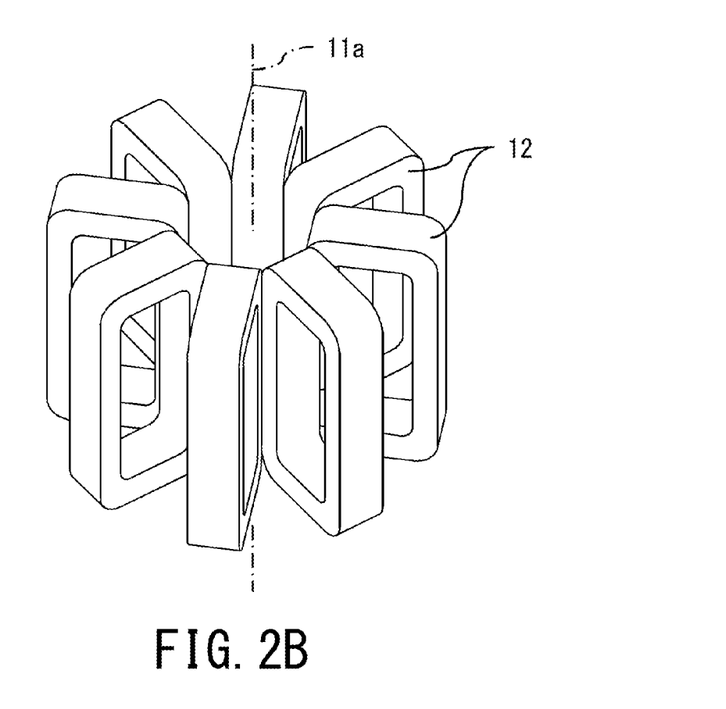

In some cases, as shown in FIG. 2(A) and FIG. 2(B), the distal end portion of the probe is configured such that the coils 12 are radially arranged so that the central axis of the element wire-winding of each of the coils 12 is arranged in a twist pattern to be perpendicular to but not to intersect the axis 11a of the probe. In this case, the symmetrical axis of the coils 12, which are arranged annularly, is the probe axis 11a.

Alternatively, in other cases, although not shown, the distal end portion of the probe is configured such that the central axis of the element wire-winding of each of the coils 12 is arranged in parallel relationship with the axis 11a of the probe.

When the AC power source 14 generates an AC voltage, an excitation magnetic field is generated in the excitation coil 12a, and an eddy current is excited in the inspection object 13.

Then, when an induction magnetic field generated by the eddy current interlinks the detection coil 12b, an induced electromotive voltage is generated in the detection coil 12b.

Then, when, while being scanned on the surface of the inspection object 13, the coils 12 and 12 pass through the vicinity of a flaw, the eddy current flows to bypass the flow. Thereby, the distribution of the induction magnetic field is changed, and the induced electromotive voltage generated in the detection coil 12b is also changed.

The detecting section 15 outputs, as a detection signal, the change of the induced electromotive voltage which is generated in the detection coil 12b by the induction magnetic field of the eddy current.

The detecting sections 15 and 15 are provided to respectively correspond to the coils 12 and 12.

Figure 3:
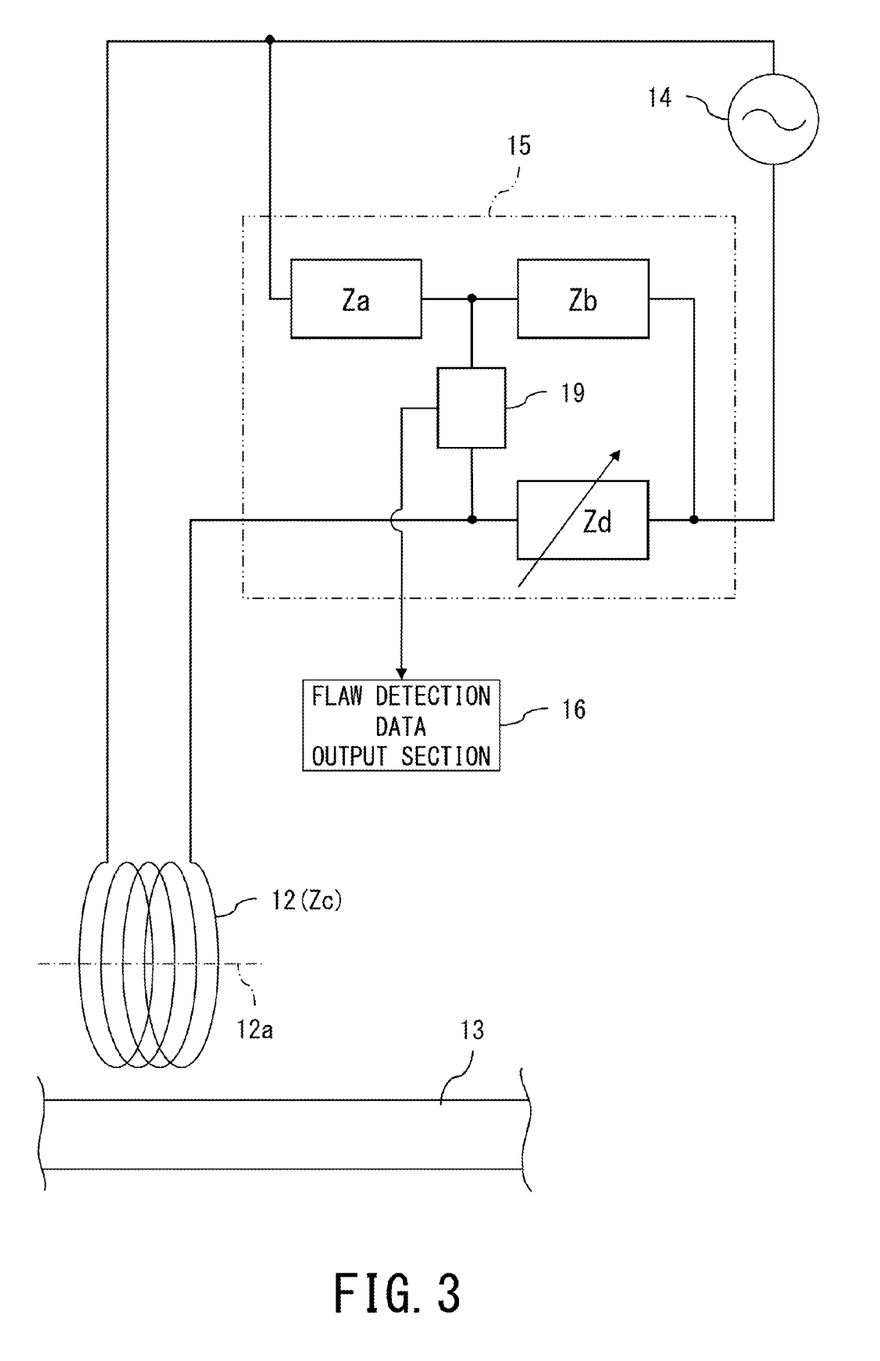
FIG. 3 is a detail view of a detecting section in the eddy current flaw detection apparatus according to the embodiment.

As shown in FIG. 3, each of the detecting section 15 is configured by a bridge circuit formed by four inductors Za, Zb, Zc and Zd and by the coil 12.

When the following expression (1) is established, the bridge circuit is maintained in a state of balanced equilibrium, and hence no current flows through an amplifier circuit 19.

$$Za \times Zd = Zb \times Zc \quad (1)$$

The operation of the detecting section 15 will be described based on FIG. 3.

When the AC power source 14 is operated to generate an excitation magnetic field in the coil 12, an eddy current is excited in the inspection object 13. Then, when an induction magnetic field generated by the eddy current interlinks the coil 12, an induced electromotive voltage is generated in the coil 12.

In the state in which the coil 12 is scanned close to an inspection surface without flaw, the excitation magnetic field is generated to adjust the variable inductor Zd so that the state of balanced equilibrium is maintained in the bridge circuit.

Further, when the coil 12 is scanned to pass through the vicinity of a flaw, the eddy current flows to bypass the flow to change the distribution of the induction magnetic field, and thereby the induced electromotive voltage of the coil 12 is also changed.

Since the balanced equilibrium of the bridge circuit is not maintained due to the impedance change of the coil 12 (Zc), the amplifier circuit 19 detects a current.

The current detected by the amplifier circuit 19 is inputted, as a detection signal, into the flaw-detection-data output section 16.

It should be noted that, as the configuration of the detecting section 15, for example, any configuration can be suitably adopted as long as the configuration is capable of detecting an impedance change of each of the coils 12 during the scanning.

As described above, a flaw detection method is exemplified based on a self-induction method in which the generation of an eddy current by an excitation magnetic field, and the detection of an induction magnetic field generated by the eddy current are performed by the one single coil 12.

However, the flaw detection method is not limited to the self-induction method, and it is also possible to adopt a mutual induction method in which the excitation coil 12a and the detection coil 12b are realized by separate coils. Alternatively, it is also possible to perform a flaw detection test in which the self-induction method and the mutual induction method are switched.

Further, in the above, the coils 12 are connected in parallel to the AC power source 14, but there is also a case in which the coils 12 are connected in series to the AC power source 14.

Returning to FIG. 1, the description of the eddy current flaw detection apparatus is continued.

The output section 16 receives the detection signals respectively outputted from the detecting sections 15 and 15, and outputs flaw detection data obtained by suitably arithmetically processing the received signals. Then, the display section 21 displays the flaw detection data outputted by the output section 16.

The flaw detection data provide accurate information about the presence or absence of a flaw under the premise that the probe axis 11a and the surface normal 13a of the inspection object (see FIG. 4(A)) are always matched to one another (inclination angle θ=0) during the scanning.

For this reason, at the time when flaw detection is performed on a complicated surface whose shape changes three-dimensionally, it is easy that the probe axis 11a and the surface normal 13a of the inspection object are not matched to one another (inclination angle θ≠0), and hence, the accuracy of the information about the presence or absence of a flaw is lowered.

The storage section 17 mutually associates and stores the detection signals detected at the same time from the plurality of detection coils 12b and 12b.

The plurality of detection signals, which are detected at the same timing to be associated with each other, coincide with each other at the time when the probe axis 11a and the surface normal 13a of the inspection object are matched to each other (inclination angle θ=0). However, the plurality of detection signals do not coincide with each other at the time when the probe axis 11a and the surface normal 13a of the inspection object are not matched to each other (inclination angle θ≠0). Further, according to the direction and magnitude of the inclination angle θ, the values of the plurality of detection signals are variously changed.

The evaluating section 18 acquires, from the storage section 17, the detection signals at a timing specified by operator's operation from an input section 22, and makes the acquired detection signals displayed on the display section 21.

Based on the detection signals displayed on the display section 21, the operator can evaluate the attitude of the probe 11 at the same time as the operation.

Further, based on the acquired detection signals, the evaluating section 18 derives the inclination angle θ and the inclination direction of the probe axis 11a with respect to the surface normal 13a of the inspection object, and evaluates the attitude of the probe by using the inclination angle and the inclination direction.

The outline of derivation of the inclination angle θ and the inclination direction (a to h) of the probe axis 11a will be described based on FIG. 4. It should be noted that the description is based on the premise that the eddy current flaw detection apparatus is configured such that the coils 12A and 12B can be respectively used in the self-induction method, and such that the coils 12A and 12B can be combined to operate in the mutual induction method.

Figure 4B:
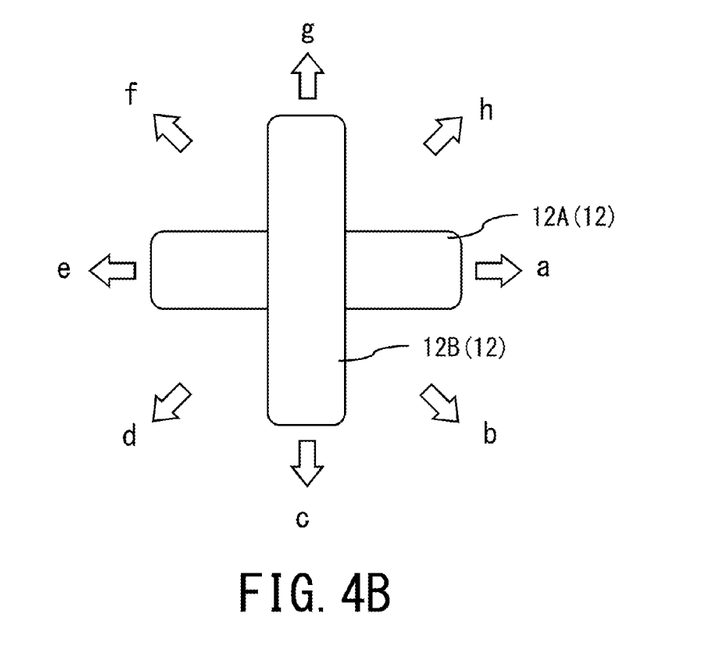
FIG. 4B is a top view of the coil for explaining the attitude of the probe.

The inclination shown in FIG. 4(A) is defined to correspond to the inclination direction a in FIG. 4(B), and the other different inclination directions b to h are similarly defined.

Further, it is assumed that, when the inclination angle of the probe axis 11a is 0, the relative positional relationships of the coils 12A and 12B with respect to the inspection object 13 are the same, and hence, the induced electromotive voltages of the respective coils 12 are equal to each other.

Next, when the coil 12 is inclined in the inclination direction a, the relative positional relationship between the coil 12A and the inspection object 13 is different from the relative positional relationship between the coil 12B and the inspection object 13, and hence the induced electromotive voltage of the coil 12A is different from the induced electromotive voltages of the coil 12B.

Figure 7:
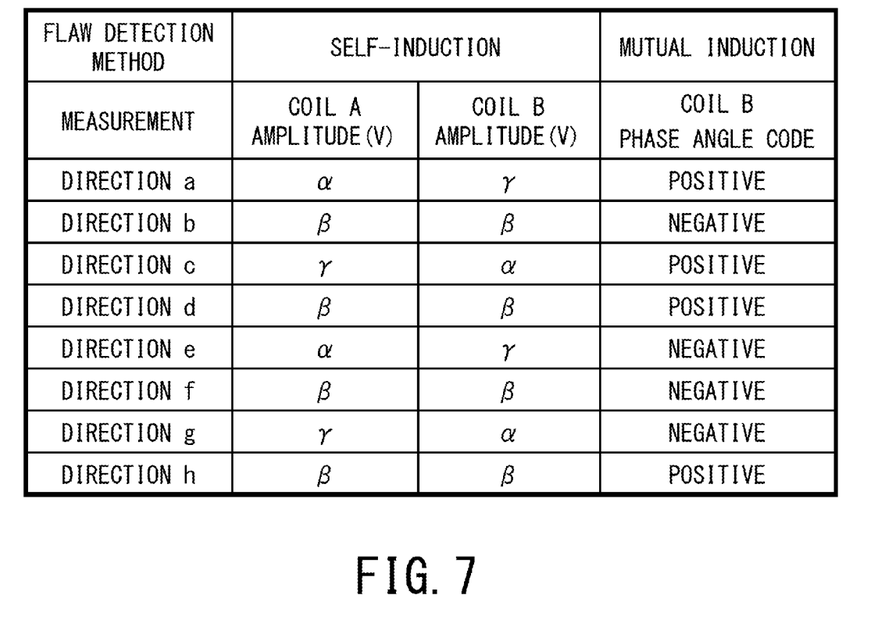
FIG. 7 is a table showing detection results corresponding to the inclined directions of the probe.

A table in FIG. 7 shows the amplitude of each of the voltage signals detected by the coil 12A (coil A) and the coil 12B (coil B) in the self-induction method in the state where the probe 11 is inclined in each of the directions (a to h), and also shows a phase angle sign (positive or negative) of the voltage signal detected by the coil 12B when the self-induction method is switched to the mutual induction method in which the coil 12A is operated as an excitation coil, and in which the coil 12B is operated as a detection coil.

As shown in the table, when the inclination direction is changed, the combination of the amplitudes of the voltage signals and the phase angle sign is changed, and hence, it is possible to evaluate the inclination direction of the coil 12 based on the combination of the amplitudes and the phase angle code.

However, the difference between the direction b and the direction f, and the difference between the direction d and the direction h cannot be distinguished.

Figure 8:
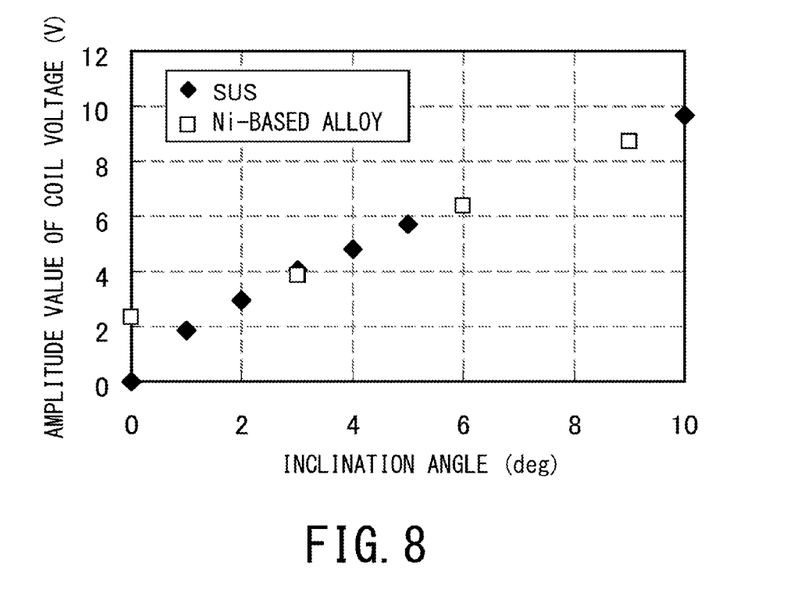
FIG. 8 is a graph in which the amplitude voltages of the coil operated in the self-induction method are shown with respect to the inclination angle of the probe.

In a graph in FIG. 8, the amplitude of the voltage of the coil 12A in the self-induction method is shown with respect to the inclination angle of the probe 11.

From the graph, it is seen that, in the range of the inclination angle from 0 to 10 degrees, the amplitude is increased monotonically with increase of the inclination angle.

In this way, when data of the relationship between each of the amplitude of voltage and the inclination angle θ in each of the coils 12A and 12B is obtained beforehand, the inclination angle θ can be derived quantitatively from the amplitude of the detected voltage.

Further, the position coordinates of the probe 11 actually in contact with the inspection object 13 can be obtained from the evaluation results of the inclination direction and the inclination angle of the probe 11, the shape of the probe, the position coordinates at which flaw detection data are to be acquired at the beginning, and respective axis positions of an access apparatus (FIG. 5), such as a robot arm (described below).

The graph in FIG. 8 shows the relationship between the inclination angle and the voltage amplitude value of each of inspection objects 13 having different materials (SUS and Ni-based alloy).

In this way, the difference in the relationship between the inclination angle and the voltage amplitude value, which difference depends on the material of the inspection object 13, is remarkable in particular in a region in which the inclination angle is small.

For this reason, the quantitative accuracy of the inclination angle θ can be improved in such a way that data of the relationship between the inclination angle and the voltage amplitude value of each of the coils 12A and 12B are obtained beforehand for each material of the inspection object 13.

In this way, in the present embodiment, the attitude of the probe 11 can be evaluated based on the detection signal of each of the coils 12A and 12B provided in the probe 11.

For this reason, it is possible to detect the amount of positional differences from the position coordinates of the inspection object 13 at which flaw detection data are to be initially acquired.

Further, since the sensing surface of the distal end of the probe can be formed small, it is possible to perform flaw detection of a narrow portion having a small curvature radius.

Second Embodiment

Figure 5:
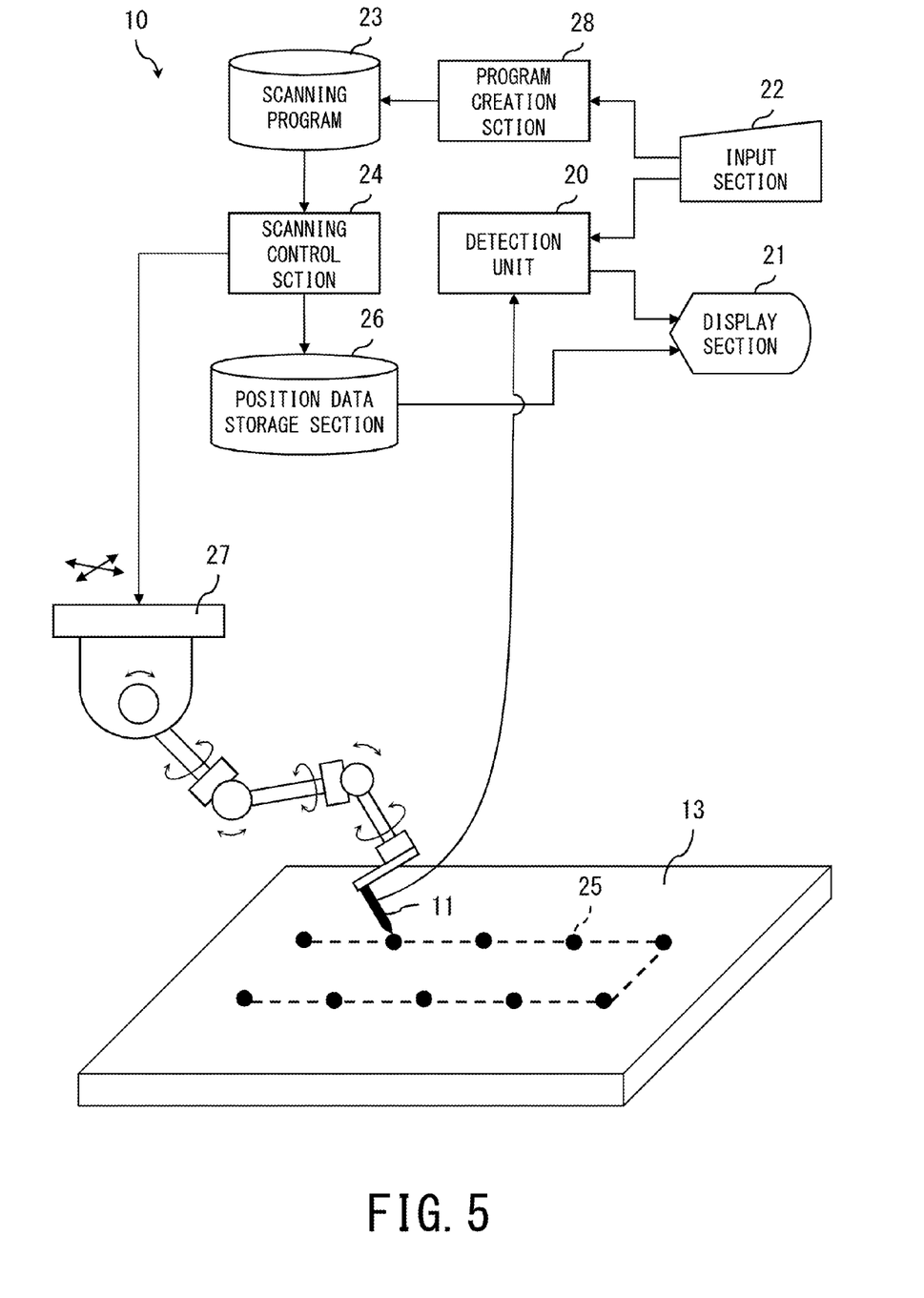
FIG. 5 is a schematic diagram showing a second embodiment of the eddy current flaw detection apparatus according to the present invention.

Next, a second embodiment of the present invention will be described based on FIG. 5. It should be noted that, in FIG. 5, portions having the same configurations or the same functions as those in FIG. 1 are denoted by the same reference numerals, and the description thereof is omitted.

An eddy current flaw detection apparatus 10 of the second embodiment includes, in addition to the detection unit 20 (FIG. 1), a control section 24 scanning the probe 11 based on a scanning program 23, and a storage section 26 mutually associating and storing the detection signals and position data 25 on the inspection object 13, the position data 25 being outputted at the same timing as that of the detection signals.

In the control section 24, the probe 11 is mounted to an articulated robot 27 by which the probe 11 is scanned on the surface of the inspection object 13 based on the scanning program 23.

Trajectory data of the position data 25 on the inspection object 13 scanned by the probe 11 are inputted into the scanning program 23.

The position data 25 on the inspection object 13, which are obtained by the articulated robot 27 scanning the surface of the inspection object 13, are stored in the storage section 26 by being associated with the detection signals which are outputted at the same timing from the probe 11 and processed in the detection unit 20.

Thereby, in consideration of the relationship between the evaluation results obtained by the probe attitude evaluating section 18 and the corresponding position data 25, it is possible to re-evaluate the reliability of the flaw detection data based on the position data 25.

As a result, it is worried that the reliability of the flaw detection data is reduced due to the attitude of the probe. In this case, the scanning program 23 is reconfigured in a program creation section 28, and again, the control section 24 is operated.

Figure 6:
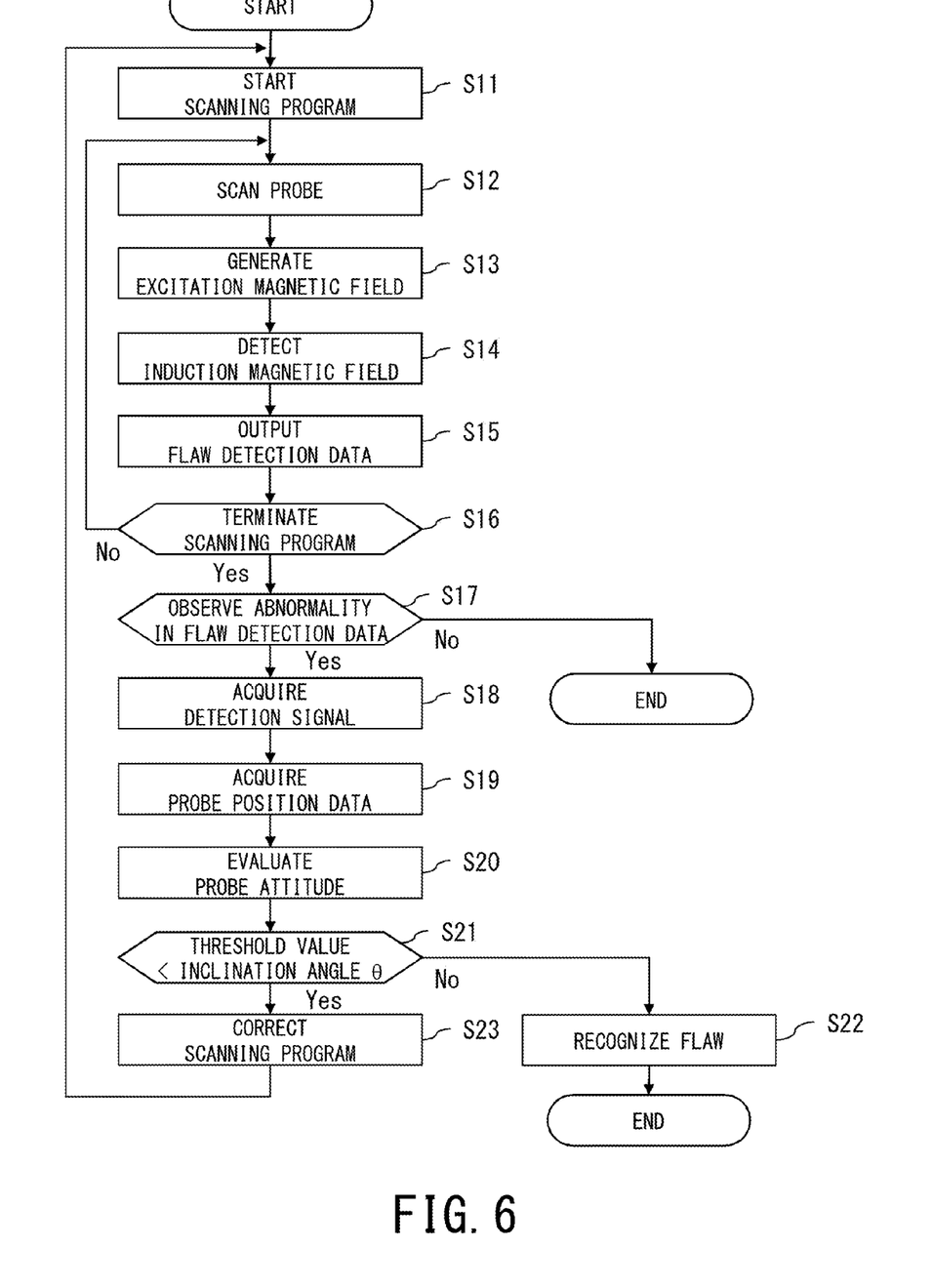
FIG. 6 is a flow chart explaining an operation of the eddy current flaw detection apparatus according to the embodiment.

The operation of the eddy current flaw detection apparatus according to the embodiment will be described based on a flow chart in FIG. 6 (see FIG. 1 and FIG. 5 where appropriate).

Based on the scanning program provided in the eddy current flaw detection apparatus, the control section 24 of the robot 27 is started (S11), and thereby the surface of the inspection object 13 is scanned by the probe 11 (S12).

While the surface of the inspection object 13 is scanned by the probe 11 in this way, an excitation magnetic field is generated by the excitation coil 12a (S13), and thereby, an induction magnetic field induced by an eddy current excited in the inspection object 13 is detected by the detection coil (S14), and then flaw detection data are outputted (S15). This flow is repeated until the scanning program is completed (S16 Yes No).

Then, when no abnormality is observed in the outputted flaw detection data (S17 No), the scanning program is ended. On the other hand, when an abnormality is observed in the outputted flaw detection data (S17 Yes), the detection signal detected at the same time as the detection of the abnormal flaw detection data is acquires from the storage section 17 (S18), and further, the position data 25 corresponding to the abnormal flaw detection data are acquired (S19).

The attitude of the probe 11 in the corresponding position data 25 is evaluated based on the acquired detection signal (S20).

Then, when the inclination angle θ is smaller than a threshold value (S21 No), the observation results of the flaw detection data, in which the abnormality is observed, are regarded as valid, so that the presence of the flaw in the corresponding position data 25 is recognized (S22).

On the other hand, when the inclination angle θ is larger than the threshold value (S21 Yes), the observation results of the flaw detection data, in which the abnormality is observed, are regarded as invalid, the scanning program is corrected (S23), and again, the probe 11 is scanned at positions around the position data 25 in which the abnormality was observed (S12).

Then, when no abnormalities in the flaw detection data is observed (S17 No), or until the presence of a flaw is recognized (S21 No), the re-scanning of the probe is repeated while the scanning program is corrected.

With the eddy current flaw detection apparatus of at least one of the embodiments described above, it is possible to evaluate the attitude of the probe based on the detection signals detected at the same timing by the plurality of detection coils, and thereby the flaw detection inspection of a narrow portion is performed with high reliability.

Although some embodiments according to the present invention have been described above, these embodiments are presented as examples, and are not intended to limit the scope of the invention. These embodiments can be implemented in other various forms, and various abbreviations, exchanges, changes and combinations can be made within a scope not deviating from the essence of the invention. These embodiments and their modifications are included in the scope and the essence of the invention, and are included in the invention described in the claims, and the equal scope thereof.

Further, the components of the eddy current flaw detection apparatus can also be realized by a processor of a computer, and can be operated by the eddy current flaw detection program.

REFERENCE SIGNS LIST

Eddy current flaw detection apparatus
11 Probe
11a Probe axis
12 (12A, 12B) Coil
12a Excitation coil
12b Detection coil
13 Inspection object
13a Surface normal
14 AC power source
15 Detecting section
16 Flaw detection data output section (output section)
17 Detection signal storage section (storage part)
18 Probe attitude evaluating section (evaluating section)
19 Amplifier circuit
20 Detection unit
21 Display section
22 Input section
23 Scanning program
24 Scanning control section (control unit)
25 Position data
26 Position data storage section (storage section)
27 Articulated robot
28 Program creation section

The invention claimed is:
1. An eddy current flaw detection apparatus comprising:
an AC power source configured to generate an excitation magnetic field in each of a plurality of coils accommodated in a probe to excite an eddy current in an inspection object;
a detector configured to detect a detection signal generated by an induction magnetic field induced by the eddy current in each of the plurality of coils accommodated in the probe;
an output configured to output flaw detection data based on the detection signals;
a storage configured to mutually associate and store the detection signals detected at a same time from the plurality of coils; and an evaluating circuit configured to evaluate an attitude of the probe at a detected timing based on the plurality of detection signals detected using the detector and mutually associated in the storage, wherein:

each of the plurality of coils accommodated in the probe is configured to be enabled to detect a flaw in a self-induction mode, where each of the plurality of coils serves as both an excitation coil and a detection coil, the plurality of coils accommodated in the probe are configured to be enabled to detect the flaw in a mutual induction mode, where at least one of the coils is operated as the detection coil, and the evaluating circuit is configured to evaluate the attitude of the probe based on switching between an amplitude detected with the coils in the self-induction mode and a positive-or-negative of a phase detected with the coils upon switching to the mutual-induction mode.

2. The eddy current flaw detection apparatus according to claim 1, further comprising:

a control section configured to scan the probe based on a scanning program, wherein:

the storage section is configured to mutually associate and store the detection signals and position data on the inspection object, the position data being outputted at the same time as the detection signals.

3. The eddy current flaw detection apparatus according to claim 1, wherein each of the plurality of coils is arranged to have a central axis perpendicular to an axis of the probe.

4. The eddy current flaw detection apparatus according to claim 1, wherein the attitude of the probe is expressed by an inclination angle and an inclination direction of the axis of the probe with respect to a normal of the inspection object.

5. An eddy current flaw detection method comprising:

generating an excitation magnetic field in each of a plurality of coils accommodated in a probe to excite an eddy current in an inspection object;

detecting a detection signal generated by an induction magnetic field induced by the eddy current in each of the plurality of coils accommodated in the probe;

outputting flaw detection data based on the detection signals;

mutually associating and storing the detection signals detected at a same time from the plurality of coils;

evaluating an attitude of the probe at a detected timing based on the plurality of detection signals detected and mutually associated and stored;

detecting a flaw in a self-induction mode using each of the plurality of coils accommodated in the probe, where each of the plurality of coils serves as both an excitation coil and a detection coil; and detecting the flaw in a mutual induction mode using each of the plurality of coils, where at least one of the coils is operated as the detection coil, wherein the evaluating the attitude of the probe is based on switching between an amplitude detected with the coils in the self-induction mode and a positive-or-negative of a phase detected with the coils upon switching to the mutual-induction mode.

6. A non-transitory computer-readable storage medium storing computer-readable instructions that, when executed by a computer, cause the computer to perform a method for detecting an eddy current flaw comprising:

generating an excitation magnetic field in each of a plurality of coils accommodated in a probe to excite an eddy current in an inspection object;

detecting a detection signal generated by an induction magnetic field induced by the eddy current in each of the plurality of coils accommodated in the probe;

outputting flaw detection data based on the detection signals;

mutually associating and storing the detection signals detected at a same time from the plurality of coils;

evaluating an attitude of the probe at a detected timing based on the plurality of detection signals detected and mutually associated and stored;

detecting a flaw in a self-induction mode using each of the plurality of coils accommodated in the probe, where each of the plurality of coils serves as both an excitation coil and a detection coil; and detecting the flaw in a mutual induction mode using each of the plurality of coils, where at least one of the coils is operated as the detection coil, wherein the evaluating the attitude of the probe is based on switching between an amplitude detected with the coils in the self-induction mode and a positive-or-negative of a phase detected with the coils upon switching to the mutual-induction mode.

* * * * *